United States Patent [19]

Winer et al.

[11] Patent Number: 4,564,365
[45] Date of Patent: Jan. 14, 1986

[54] QUICK CHANGE MECHANISM FOR A LIMB PROSTHESIS

[76] Inventors: Richard A. Winer, P.O. Box 1673, Fort Lauderdale, Fla. 33302; Kevin S. Garrison, 2301 N.W. 60th Ave., Sunrise, Fla. 33313

[21] Appl. No.: 476,704
[22] Filed: Mar. 18, 1983
[51] Int. Cl.$^4$ ............................ A61F 2/80; A61F 2/74
[52] U.S. Cl. .......................................... 623/27; 623/38
[58] Field of Search ....................... 3/2, 12, 12.2–12.8, 3/21, 22, 24

[56] References Cited

U.S. PATENT DOCUMENTS 1,380,664  6/1921  Luke ...................................... 3/12.4

FOREIGN PATENT DOCUMENTS 123348   5/1918  United Kingdom ....................... 3/21
155917  12/1920  United Kingdom ....................... 3/21

*Primary Examiner*—Ronald L. Frinks
*Attorney, Agent, or Firm*—Melvin K. Silverman

[57] ABSTRACT

A coupling system including a male element having a first end and a second end in which the first end is integrally connected to said socket portion and said second end comprises an annular, circumferential shoulder. Also included is a hollow, pipe-like female element depending from the prosthesis to be changed, and having two longitudinal side openings each on opposite side walls of said female element. In association with the female element is a pair of cam latches which are rotatably secured within said side openings of said female element. Each cam latch comprises, in combination, a convex arc and handle element disposed, with relationship to said openings, such that the selective downward rotation of said handles will bring said convex arc of said cam latch into the interior of the female element and, thereby, within the walls thereof. The circumferential shoulder of the male element may be press-fittably inserted into said side opening such that said shoulders will be engaged by the selective downward rotation of said cam latches into and against the exterior of the male element. Therein, a prosthesis which is integrally secured to the first end of the male element may be readily connected or disconnected by the respective engagement or disengagement of the male and female elements.

1 Claim, 8 Drawing Figures

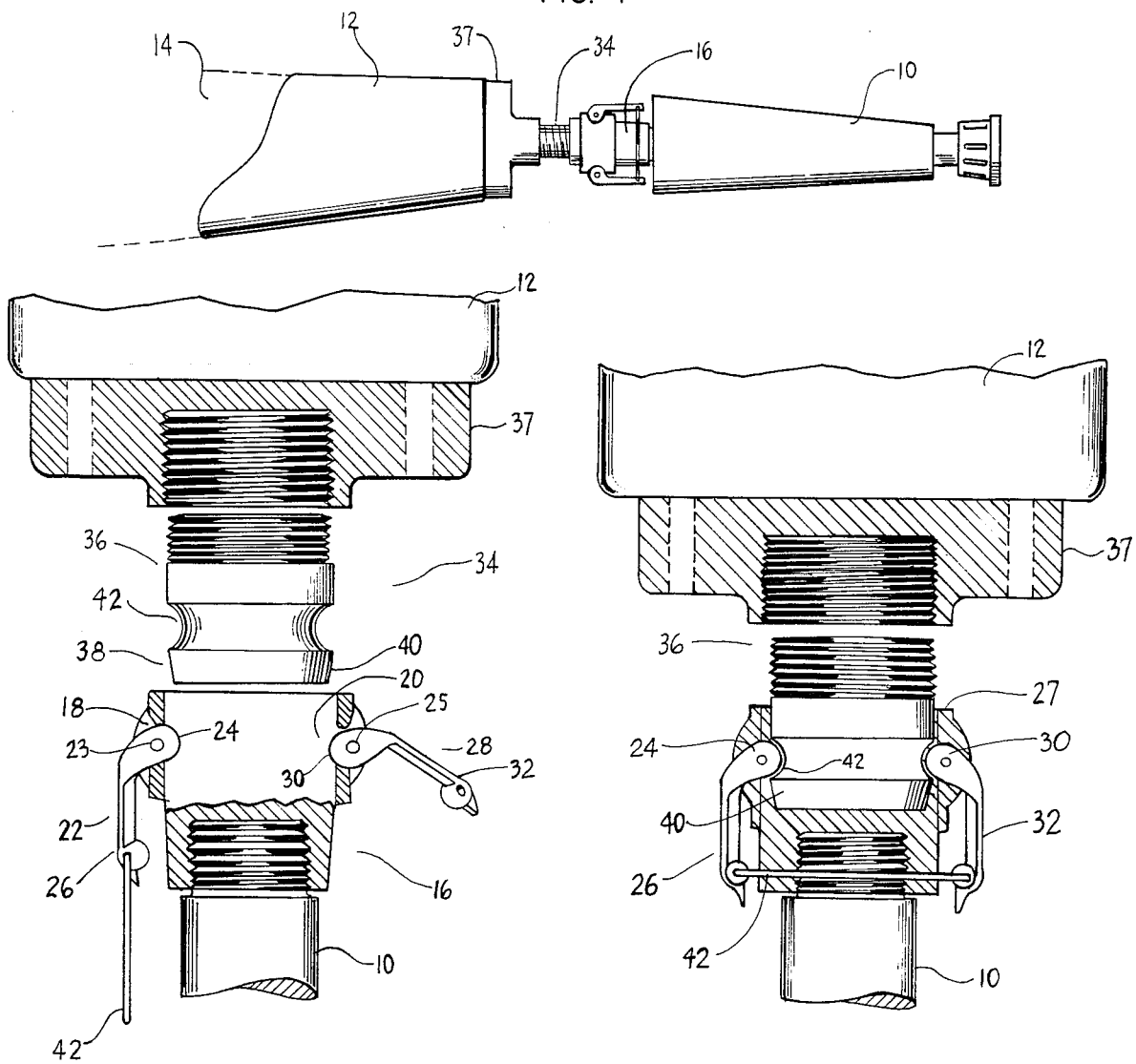
FIG. 1
FIG. 2
FIG. 3
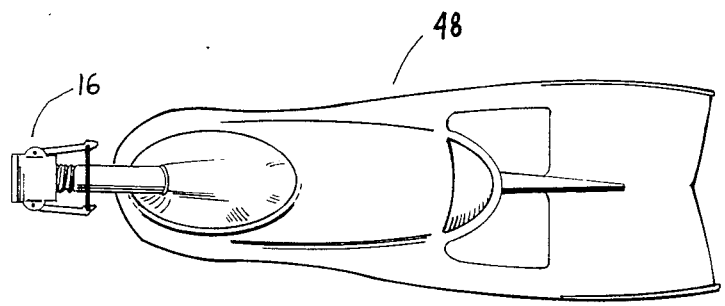
FIG. 8

QUICK CHANGE MECHANISM FOR A LIMB PROSTHESIS

BACKGROUND OF INVENTION

The present invention relates to artificial limbs and, more particularly, to an improvement in a coupling between an artifical limb and an amputation site in order to provide a simplified and expeditious change between one special purpose limb prosthesis and another.

Artificial limbs, or prostheses, have been used by amputees for many centuries. From their beginnings, they have evolved from crudely shaped sticks, pegs or hooks, into sophisticated electro-mechanical equipment, occasionally incorporating servomotors and micro-processors to produce more natural limb movement. However, even given such development, problems remain in the means for attaching and detaching a prosthesis to the amputation site.

Problems associated with the changing of the prosthesis have increased as amputees have acquired more than one prosthesis for use in differing situations and environments. Therefore, the course of development of prostheses has dictated a need for more effective means for rapidly changing from a prosthesis intended for one purpose to another prosthesis intended for use in another purpose or application.

In general, the prior art has had little to say in this area. However, relevant prior art is believed to include U.S. Pat. Nos. 3,461,464; 3,947,897; and 4,158,895. The proper area of classification is believed to be U.S. Class 3, Sub-classes 2 and 21.

SUMMARY OF THE INVENTION

The instant invention constitutes a coupling for use in the connection and disconnection of a prosthesis to a socket portion of an amputation site in which the socket portion is adapted to extend back over the human limb in order to secure the socket portion thereon. Particularly, the inventive coupling comprises a male element having a first end and a second end in which the first end is integrally connected to said socket portion and said second end comprises an anular, circumferential shoulder. A further aspect is a hollow, pipe-like female element depending from the prosthesis to be changed, and having two longitudinal side openings each on opposite side walls of said female element. In association with the female element is a pair of cam latches which are rotatably secured within said side openings of said female element. Each cam latch comprises, in combination, a convex arc and handle element disposed, with relationship to said openings, such that the selective downward rotation of said handles will bring said convex arc of said cam latch into the interior of the female element and, thereby, within the walls thereof. In the above arrangement, the circumferential shoulder of the male element may be press-fittably inserted into said side opening such that said shoulders will be engaged by the selective downward rotation of said cam latches into and against the exterior of the male element. Therein, a prosthesis which is integrally secured to the first end of the male element may be readily connected or disconnected by the respective engagement or disengagement of the male and female elements.

It is a principal object of the present invention to provide a quick-change coupling for use in the connection and disconnection of a prosthesis to a socket portion of an amputation site.

A further object is to provide a coupling means for use in a prosthesis connection which will permit movement between a bio-compatible sleeve and a socket forming a part of a connecter for securing a prosthesis to an amputed limb.

Another object of this invention is to provide a coupling arrangement which will permit the ready interchangeability between different types of leg and/or foot prostheses.

A still further object of the invention is to provide a coupling for use in association with an artificial leg or foot in which a varying leg or foot will be suitable for varying types of outdoor activity.

A yet further object is to provide a prosthetic coupling system that will afford ready removability of an accessory when the amputee is involved in an otherwise cramped environment such as a sub-compact auto.

These and yet other objects and advantages of the instant invention will become apparent from the hereinafter set forth specification, drawings, and claims.

BRIEF DESCRIPTION OF THE DRAWINGS

FIG. 1 is a perspective schematic view of the present inventive coupling system, in locked condition, showing a prosthetic accessory to an amputation site.

FIG. 2 is an exploded view showing the male and female elements to the present coupling prior to connection thereof.

FIG. 3 is a schematic view showing the present coupling after insertion of the male element into the female element.

FIG. 7 is a variant embodiment of the accessory of FIG. 5 in which, however, the embodiment of FIG. 7 is particularly adapted for use in mountain climbing activites and the like.

FIG. 8 is a perspective view of a prosthetic accessory, useable with the present invention, intended for use in swimming and aquatic activities.

DETAILED DESCRIPTION OF THE INVENTION

Figure 5:
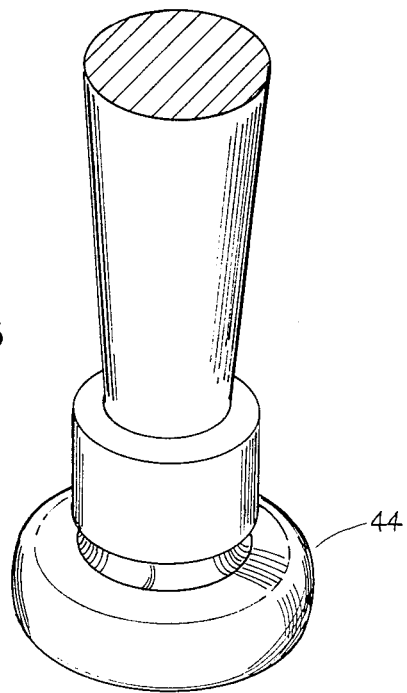

There shown in FIG. 1 a schematic perspective of the present inventive coupling and its associated environment. More particularly, there is shown a prosthesis 10 and a socket portion 12, wherein the socket portion 12 is adapted to extend back and over the amputation site of a residual 14 limb in order to secure thereto said socket portion 12.

The coupling proper comprises a hollow, pipe-like female element 16 which integrally depends from said prothesis 10. The female element is provided with two longitudinal side openings 18 and 20 disposed at opposite sides of the pipe-like female element 16 and within the walls thereof.

With further reference to FIGS. 1,2 and 3 there is shown a pair of cam latches 22 and 28 which are rotatably secured by pin connections 23 and 25 to said socket portion within a plane which is within said openings 18 and 20. Each of said cam latches 22 and 28 comprise, in combination, convex arcs 24 and 30 respectively and handles 26 and 32 respectively. These sub-elements are disposed such that the selective downward rotation of the cam latches 22 and 28 will bring said convex arcs 24 and 30 of said cam latches into said side openings 18 and 20 respectively and, thereby, within the walls of the female element 16.

Also illustrated in FIGS. 2 and 3 is male element 34 which includes a first end 36 and a second end 38, and possesses exterior dimensions that are generally complimentary to the interior dimensions of said female element 16. It is noted that the first end 36 is secured to the socket portion 12 through end plate 37, while the second end 38 of male element 34 comprises a circumferential shoulder 40. Said shoulder 40 is press-fittably insertable into said longitudinal side opening 18 and 20, as is shown in FIG. 3. The shoulder 40 is engaged by the selective downward rotation of the cam latches 22 and 28 into and against a cylindrical area 42 immediately above the circumferential shoulder 40. By such engagement, the prosthesis 10 which is integrally secured to the female element 11, may be readily connected or disconnected by the respective engagement or disengagement of the male and female elements.

Further shown in FIGS. 2 and 3 is a retainer clip 42 which is useful as a failsafe for the retention of the latches in a locked position.

By reference to FIGS. 4 through 9, it will, as hereinafter described, be appreciated that the prosthetic accessory 10 may take a wide variety of forms which, for example, can comprise particular attachments for such purposes as walking on sand (FIGS. 4, 5 and 6), mountain climbing (FIG. 7) or aquatic activities (FIGS. 8 and 9). An objective of the present invention is to provide a quick change mechanism for the athletically inclined amputee in order to permit such an individual to readily change his prosthesis in accordance with the particular activity of interest to him at a given time. This represents an advance over prior art prostheses in which the intent was merely to create a relatively permanent connection between the prosthesis and the socket portion of the amputation site.

Figure 4:
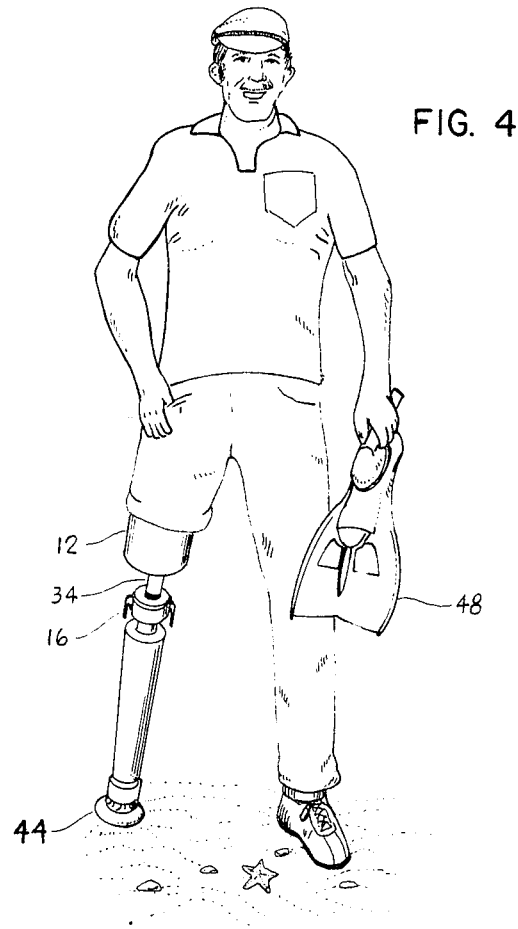
FIG. 4 is a perspective representation of a user of the present invention, utilizing the present coupling in connection with one prosthestic accessory, however, holding the embodiment of FIG. 8.
Figure 6:
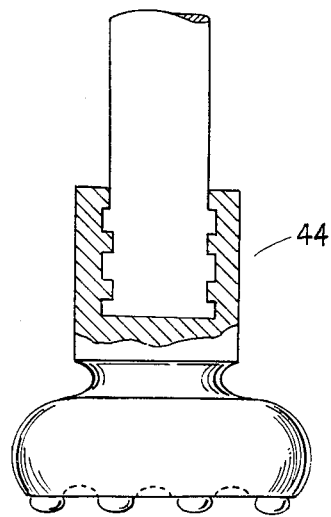
FIG. 6 is a schematic view of the prosthesis of FIG. 5.

Shown in FIG. 4 is a user of the present coupling in which a prosthesis 44 particularly adapted for walking upon sand or a similar surface is shown. FIG. 5 is an enlarged perspective of the prosthesis 44 while FIG. 6 is a cross-sectional schematic thereof.

Figure 7:
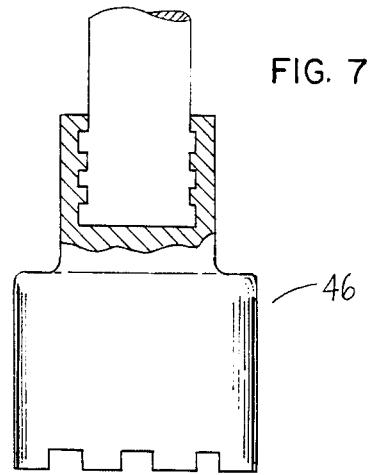

In FIG. 7 is shown a cross-sectional schematic of a prosthetic attachment 46 particularly adapted for use by amputees engaged in mountain climbing.

The prosthetic attachment 48 (shown in FIGS. 8 and 9) is particularly adapted for amputees involved in aquatic sports including scuba diving and the like.

It is to be understood that while there have been shown and described the preferred embodiments of the present invention, the invention may be embodied otherwise than as herein specifically illustrated or described and that within such embodiments certain changes in the detail of construction, or in the form and arrangements of the parts, may be made with departing from the underlying idea or principles of this invention within the scope of the appended claims.

Having thus described our invention, what we claim as new, useful and non-obvious and, accordingly, secure by Letters Patent of the United States is:

1. A coupling system for use in the connection and disconnection of a prosthetic accessory to a socket portion of a lower limb amputation site, such socket portion adapted to extend back over the lower limb to secure the socket portion thereon, the inventive coupling comprising:

(a) a hollow, pipe-like female element integrally depending from said prosthetic accessory, said female element having two longitudinal side openings, each within opposite walls of said female element;

(b) a pair of cam latches rotatably secured within said longitudinal side openings, such cam latches comprising, in combination, a convex arc and handle element disposed in a plane wherein the selective downward rotation of said latches will bring said convex arc of said cam latches into said side openings and, thereby, within the walls of said female element; and (c) a male element having a first end and a second end, said first end integrally secured to said socket portion and said second end comprising an annular, circumferential shoulder, the exterior dimensions of said male element, being generally complimentary to the interior dimensions of said female element, said second end of said male element being press-fittably insertable into said longitudinal side openings of said female element, said male element being radially rotationally adjustable relative to said female element prior to locking of the cam latches, wherein said male element may then be securably engaged to thereby achieve both radial and longitudinal engagement between said male and female elements by said selective downward rotation of said cam latches.

whereby, the lower extremity prosthetic accessory integrally secured to said female element may be readily connected or disconnected by the engagement or disengagement of the male and female elements through the selective locking of said cam latches.

* * * * *